US 6,641,556 B1

(12) United States Patent
Shigezawa

(10) Patent No.: US 6,641,556 B1
(45) Date of Patent: Nov. 4, 2003

(54) INTRAVENOUS FLUID HEATING SYSTEM

(75) Inventor: Gordon Shigezawa, Irvine, CA (US)

(73) Assignee: Respiratory Support Products, Inc., Irvine, CA (US)

( * ) Notice: Subject to any disclaimer, the term of this patent is extended or adjusted under 35 U.S.C. 154(b) by 0 days.

(21) Appl. No.: 09/347,778

(22) Filed: Jul. 6, 1999

(51) Int. Cl.[7] ............................. H05B 1/02; A61F 7/12
(52) U.S. Cl. ................................... 604/113; 604/93.01
(58) Field of Search ...................... 604/6.13, 93.01, 604/113, 114, 523, 537, 247, 80, 82, 84, 85

(56) References Cited

U.S. PATENT DOCUMENTS

| | | | |
|---|---|---|---|
| 623,022 A | | 4/1899 | Johnson |
| 1,572,300 A | | 2/1926 | Max |
| 1,794,215 A | | 2/1931 | Titus |
| 3,557,786 A | * | 1/1971 | Barr et al. .................. 128/214 |
| 3,584,770 A | * | 6/1971 | Taylor ......................... 222/479 |
| 3,832,998 A | * | 9/1974 | Gregg ..................... 128/214 E |
| 3,871,373 A | | 3/1975 | Jackson |
| 3,931,818 A | * | 1/1976 | Goldowsky ............. 128/214 C |
| 4,000,341 A | | 12/1976 | Matson |
| 4,038,519 A | | 7/1977 | Foucras |
| 4,091,810 A | * | 5/1978 | Lundquist ............... 128/214 R |
| 4,105,028 A | * | 8/1978 | Sadlier et al. .......... 128/214 E |
| 4,200,095 A | * | 4/1980 | Reti ........................ 128/214 C |
| 4,227,525 A | * | 10/1980 | Lundquist ............... 128/214 R |
| 4,233,973 A | * | 11/1980 | Shukla .................... 128/214 R |
| 4,249,923 A | | 2/1981 | Walda |
| 4,259,187 A | * | 3/1981 | DeFrank et al. ............. 210/446 |
| 4,308,866 A | * | 1/1982 | Jelliffe et al. ............ 128/214 E |
| 4,451,255 A | * | 5/1984 | Bujan et al. ................. 604/157 |
| 4,465,471 A | * | 8/1984 | Harris et al. .................. 604/56 |
| 4,476,685 A | | 10/1984 | Aid |
| 4,490,140 A | * | 12/1984 | Carr et al. ..................... 604/65 |
| 4,498,901 A | * | 2/1985 | Finch ........................... 604/65 |
| 4,511,353 A | * | 4/1985 | Theeuwes ..................... 604/85 |
| 4,532,414 A | | 7/1985 | Shah et al. |
| 4,552,555 A | * | 11/1985 | Theeuwes ..................... 604/56 |
| 4,586,922 A | * | 5/1986 | Theeuwes ..................... 604/85 |
| 4,650,464 A | * | 3/1987 | Ruiz et al. .................... 604/49 |
| 4,682,010 A | | 7/1987 | Drapeau et al. |
| 4,684,364 A | * | 8/1987 | Sawyer et al. .............. 604/123 |
| 4,686,354 A | | 8/1987 | Makin |
| 4,705,508 A | | 11/1987 | Karnavas et al. |
| 4,708,831 A | | 11/1987 | Elsworth et al. |

(List continued on next page.)

FOREIGN PATENT DOCUMENTS

| | | | | |
|---|---|---|---|---|
| DE | 19803378 | | 8/1998 | |
| DE | 19716977 | | 11/1998 | |
| EP | 296777 | | 12/1988 | |
| JP | 06030997 A | * | 2/1994 | .......... A61M/5/168 |
| WO | 9611027 | | 4/1996 | |

Primary Examiner—Henry Bennett

(57) ABSTRACT

A medical tubing is used for heating an intravenous fluid immediately prior to the fluid's introduction into a patient. The medical tubing comprises an internal web with a heating element along a length of the web, which heats fluid passing through the tubing. Temperature sensors at an entrance and exit of the tubing communicate the temperatures of the unheated and heated fluid, which provides a feedback control circuit for regulating the amount of heat delivered to the fluid. Current carrying wires in the web dissipate heat and thereby heat the web, which in turn heats the fluid in the tubing. A heat controlling unit adjusts an electrical current transmitted to the current carrying wires in the web. The web may be formed separately from the tubing and subsequently inserted therein, or formed integrally with the tubing by, for example, an extruding process. The web is of sufficient thickness to carry the heating element and additionally carry a separate line for the temperature signals, yet remain flexible so that the tubing can be used in the traditional manner.

5 Claims, 5 Drawing Sheets

U.S. PATENT DOCUMENTS

| | | | |
|---|---|---|---|
| 4,722,732 A | * 2/1988 | Martin | 604/132 |
| 4,740,103 A | * 4/1988 | Theeuwes | 604/83 |
| 4,740,197 A | * 4/1988 | Theeuwes | 604/84 |
| 4,740,198 A | * 4/1988 | Theeuwes | 604/84 |
| 4,740,199 A | * 4/1988 | Theeuwes | 604/84 |
| 4,740,200 A | * 4/1988 | Theeuwes | 604/85 |
| 4,740,201 A | * 4/1988 | Theeuwes | 604/85 |
| 4,741,735 A | * 5/1988 | Theeuwes | 604/85 |
| 4,756,706 A | * 7/1988 | Kerns et al. | 604/66 |
| 4,773,410 A | 9/1988 | Blackmer et al. | |
| 4,820,269 A | * 4/1989 | Riddell | 604/85 |
| 4,892,524 A | * 1/1990 | Smith | 604/246 |
| 4,955,883 A | 9/1990 | Nevyas et al. | |
| 4,962,761 A | 10/1990 | Golden | |
| 4,967,744 A | 11/1990 | Chua | |
| 4,969,871 A | * 11/1990 | Theeuwes et al. | 604/80 |
| 4,969,872 A | * 11/1990 | Urquhart et al. | 604/85 |
| 4,973,307 A | * 11/1990 | Theeuwes | 604/85 |
| 4,985,016 A | * 1/1991 | Theeuwes et al. | 604/85 |
| 4,994,031 A | * 2/1991 | Theeuwes | 604/85 |
| 5,024,657 A | * 6/1991 | Needham et al. | 604/85 |
| 5,027,809 A | 7/1991 | Robinson | |
| 5,045,059 A | * 9/1991 | Theeuwes et al. | 604/82 |
| 5,106,373 A | * 4/1992 | Augustine et al. | 604/113 |
| 5,108,372 A | * 4/1992 | Swenson | 604/113 |
| 5,154,661 A | 10/1992 | Higgins | |
| 5,160,320 A | * 11/1992 | Yum et al. | 604/85 |
| 5,172,686 A | 12/1992 | Anthony | |
| 5,180,896 A | 1/1993 | Gibby et al. | |
| RE34,365 E | * 8/1993 | Theeuwes | 604/85 |
| 5,234,414 A | * 8/1993 | Hung | 604/254 |
| 5,242,392 A | * 9/1993 | Vaughn | 604/80 |
| 5,246,438 A | 9/1993 | Langberg | |
| 5,249,585 A | 10/1993 | Turner et al. | |
| 5,250,028 A | * 10/1993 | Theeuwes et al. | 604/85 |
| 5,269,749 A | 12/1993 | Koturov | |
| 5,322,057 A | 6/1994 | Raabe et al. | |
| 5,357,948 A | 10/1994 | Eilentropp | |
| 5,362,310 A | 11/1994 | Semm | |
| 5,399,171 A | * 3/1995 | Bowman et al. | 604/247 |
| 5,433,708 A | 7/1995 | Nichols et al. | |
| 5,460,628 A | 10/1995 | Neuwirth et al. | |
| 5,492,529 A | 2/1996 | Neuwirth et al. | |
| 5,537,996 A | 7/1996 | McPhee | |
| RE35,501 E | 5/1997 | Ross et al. | |
| 5,713,864 A | 2/1998 | Verkaart | |
| 5,713,865 A | * 2/1998 | Manning et al. | 604/122 |
| 5,827,244 A | * 10/1998 | Boettger | 604/283 |
| 5,830,180 A | * 11/1998 | Chandler et al. | 604/65 |
| 5,954,313 A | * 9/1999 | Ryan | 251/149.1 |
| 6,013,060 A | * 1/2000 | Woodard | 604/246 |
| 6,068,617 A | * 5/2000 | Richmond | 604/255 |
| 6,071,262 A | * 6/2000 | Okamoto et al. | 604/82 |
| 6,167,883 B1 | * 1/2001 | Beran et al. | 128/203.17 |
| 6,186,977 B1 | * 2/2001 | Andrews et al. | 604/67 |
| 6,210,361 B1 | * 4/2001 | Kamen et al. | 604/82 |
| 6,464,667 B1 | * 10/2002 | Kamen et al. | 604/131 |
| 6,467,953 B1 | * 10/2002 | Faries, Jr. et al. | 374/162 |
| 6,491,679 B1 | * 12/2002 | Okamoto et al. | 604/410 |

\* cited by examiner

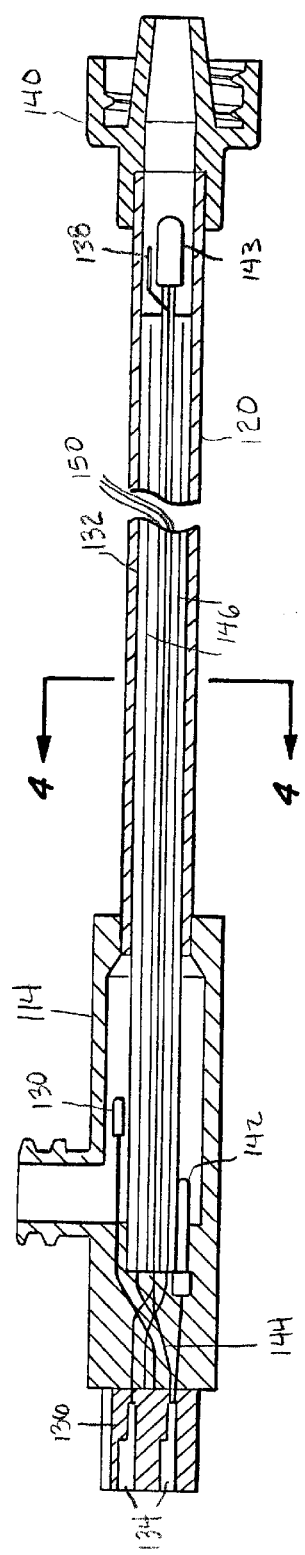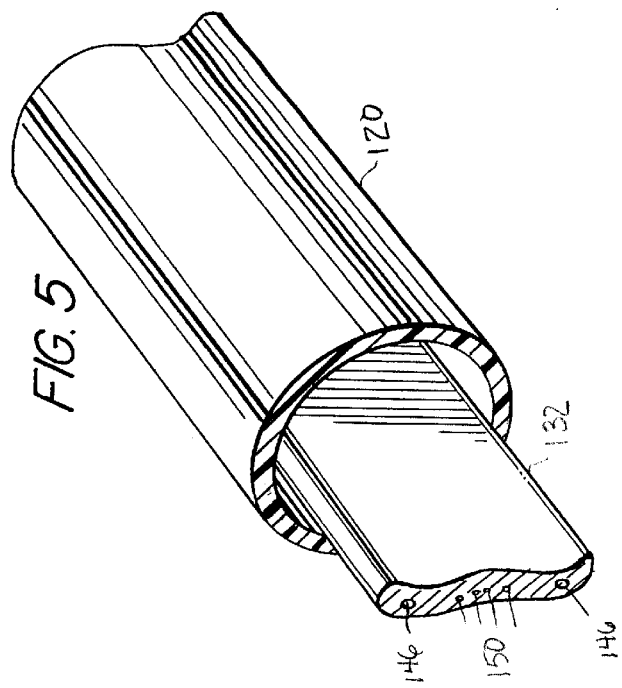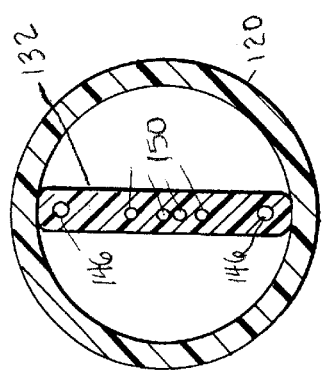

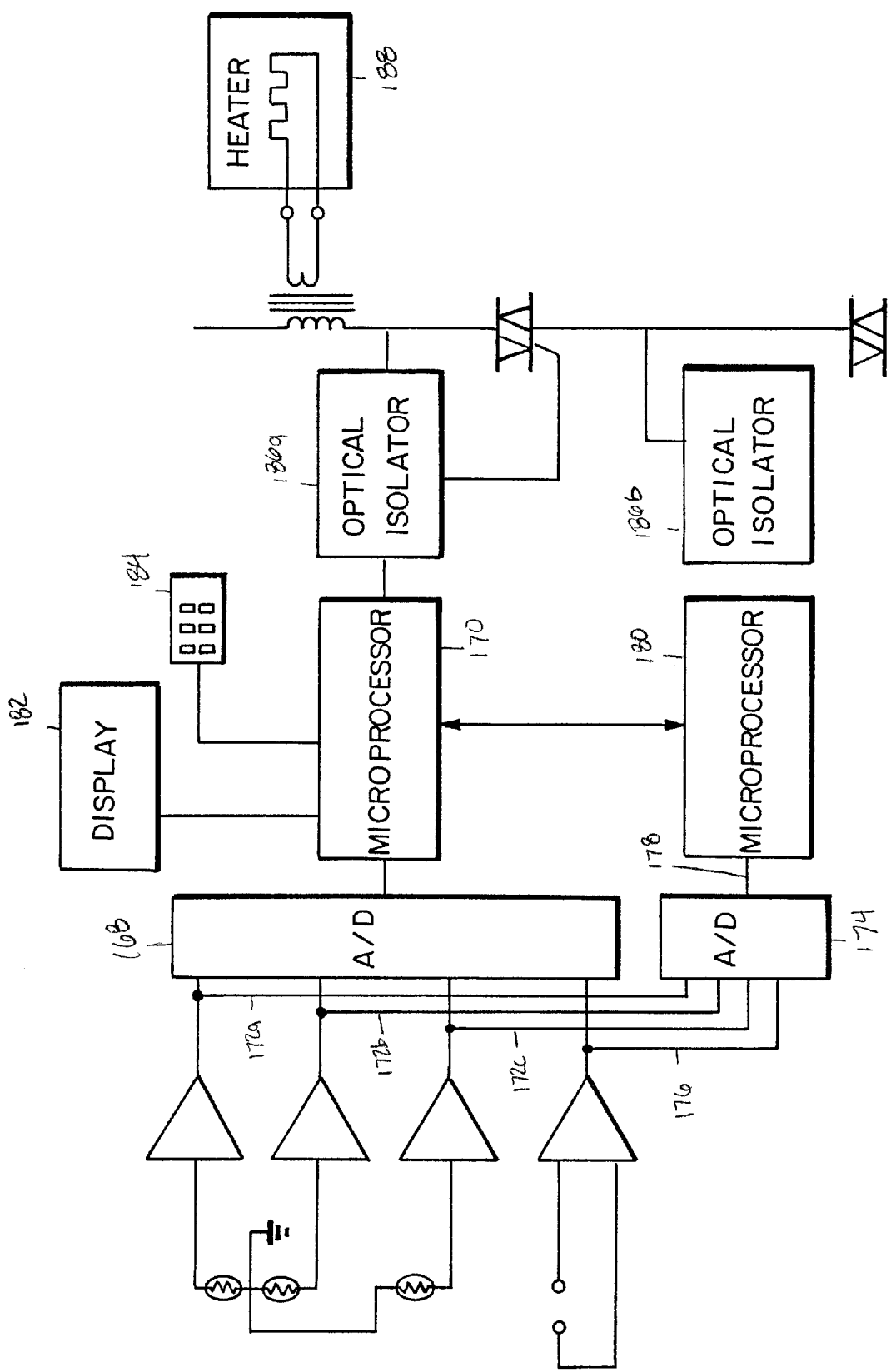

INTRAVENOUS FLUID HEATING SYSTEM

BACKGROUND OF THE INVENTION

1. Field of the Invention

The present invention relates generally to medical equipment, and more particularly to an intravenous fluid heating system including heat delivery along a length of tubing prior to introduction of the fluid into the patient to maintain and control an elevated fluid temperature.

2. Description of Related Art

Normothermia for humans is 37° C. (98.6° F.). When the body temperature falls below 36°, clinicians refer to the condition as hypothermic. Except for those rare procedures where hypothermia is a planned and carefully controlled surgical tactic for protecting the patient (e.g., open heart surgery and some neurosurgery), hypothermia is regarded as generally a disfavored, uncontrolled, and unintentional byproduct of medical procedures. However, the occurrence of hypothermia in post surgical recovery rooms can be as high as 60% to 70%. The outward manifestations of hypothermia can be shivering and discomfort, and the condition car lead to further complications.

There are many known contributing factors to post-surgical hypothermia. Cold operating rooms contribute to the patient's loss of heat. Most ORs are kept colder than normal rooms, typically maintaining a maximum temperature of 20° C. Another factor is the patient's lack of clothing during a surgical procedure. Many times a patient will be exposed to the cold operating room with at most a flimsy gown, and in some instances the patient is predominantly exposed during what can be a lengthy procedure. Evaporation of fluids applied to the body such as Iodine can further rob the patient's body of heat. Another significant loss of heat can be the heat exchange between a body which has been opened, exposing the vital organs, and the surrounding environment. These factors contribute to the high incidence of a patient's post-operative hypothermia.

An important contributor to the hypothermia problem is the introduction of intravenous (IV) fluids into the patient before, during, and after surgery. For example, blood products are stored in refrigerators at temperatures of 4° C. prior to use, which is just above freezing. Other fluids such as saline or glucose solutions are stored at room temperature (20° C.), which is approximately 17° below the body temperature. When a cold fluid is introduced into the body, the body must work to bring the new fluid to the body's operating temperature at the expense of other body functions. In doing so, the body cools below its initial temperature, with the amount of cooling dependent on the quantity and temperature of the fluid to be introduced. Large amounts of fluid or very cold fluids can cause the patient's temperature to drop several degrees, thereby triggering hypothermia even without any other contributing factors. This effect is magnified in younger patients as well as the elderly. Thus, the introduction of blood and other IV solutions are a major contributor to the problem of hypothermia in post-surgical patients.

In recognition of this problem, the medical community has tried to implement blood warmers which preheat the blood prior to introduction of the blood into the patient. However, blood warmers have heretofore been an unsatisfactory solution to the problem. First, while the existing blood warmers add some heat to the blood prior to delivery, the blood is still delivered at a temperature colder than the 37°–38° C. which is maintained by the human body. This is attributable to heat loss of the preheated blood in the line from the heater to the point of infusion, where the warm line gives off heat to the colder surrounding environment. If the flow rate of the fluid is slow, then more heat is lost during the exposure time between the heater and the infusion point.

The majority of prior art fluid warmers are limited by having the heated region separate from the point of infusion, where the heat source is separated by the venipuncture site by a length of IV tubing. The fluid cools down in the unheated line necessitating a higher initial temperature of the heated fluid. However, overheating the fluid can break down products in the fluid and in some cases render the fluid useless or unsafe. The cool-down is particularly severe at low flow rates where a long residency time in the post-heater connecting line results in heat energy loss that could be as much as the heat added. At higher flow rates, the heater response time of prior art heaters prevents rapid response to abrupt flow changes without overheating the fluid.

SUMMARY OF THE INVENTION

To offset the problem of heat loss in the tubing which transports the IV fluid from the heating unit to the patient, the present invention employs a tubing which comprises an internal heating web traversing the length of the tubing, which heats the fluid in the tubing and prevents the fluid from entering the patient below normothermia temperatures. In a preferred embodiment, the present invention includes proximal and distal sensors which evaluate the temperatures at the beginning of the tube and the point of delivery, thereby providing a feedback loop for controlling the temperature at the point of entry of the body. By placing a heating web inside the flow field of the moving fluid, the present invention advantageously heats the fluid more efficiently and more evenly than if the outer walls of the tubing were heated.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures there of, and wherein:

FIG. 3 is a schematic illustration of a length of tubing with a heating web of the present invention, shown partially in phantom;

FIG. 4 is a cross-sectional view of the tubing as depicted in FIG. 3;

FIG. 5 is an elevated, perspective view of the tubing, partially cut away, and the internal heating web of the present invention;

FIG. 7 is a block diagram of a second heater controller with dual microprocessors.

DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an IV fluid heating system with internal flow heating using an internal web to transmit heat to the moving fluid.

Figure 1:
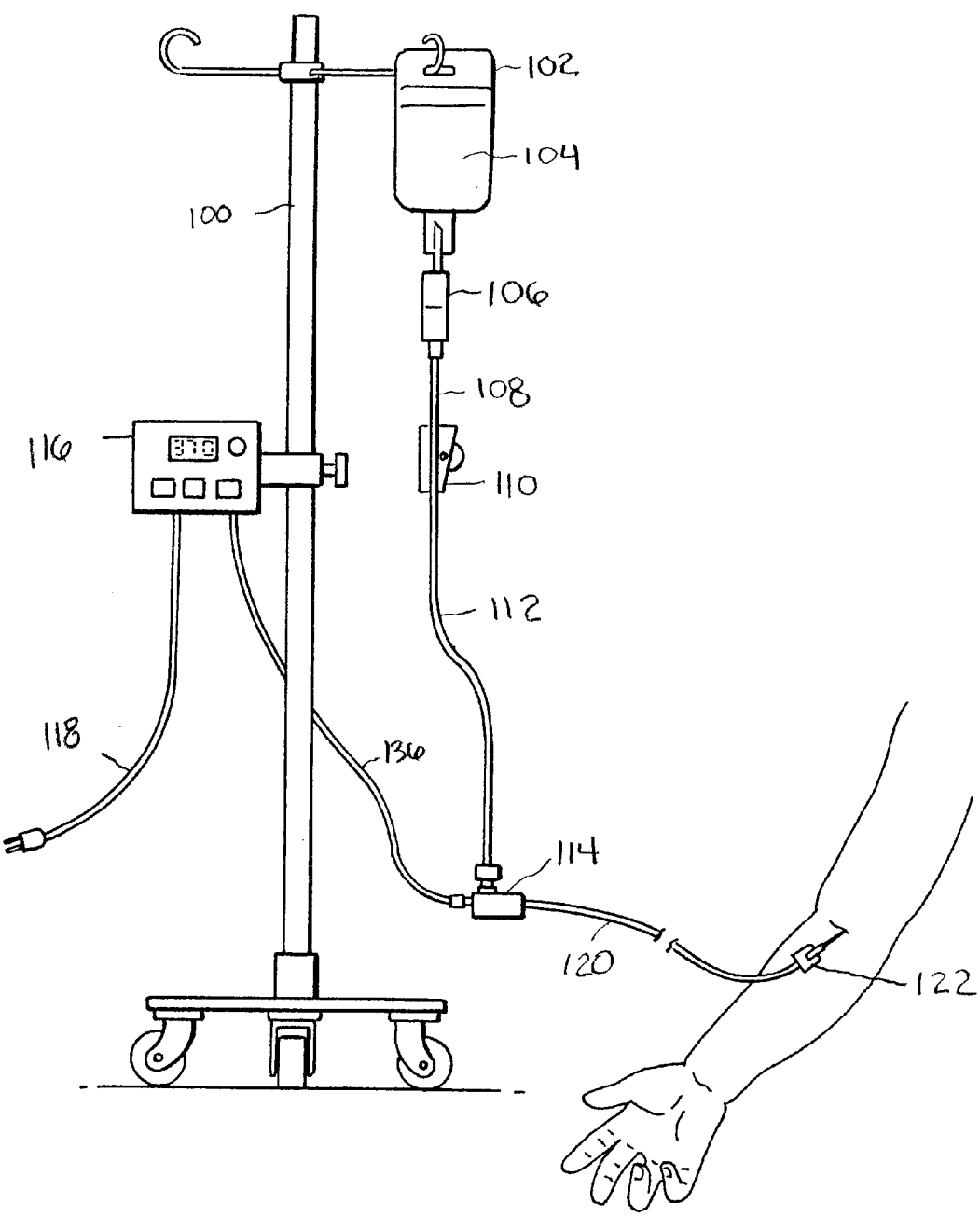
FIG. 1 is a schematic illustration of a preferred embodiment of the present invention including a gravity assisted fluid flow, a heating unit, and a length of tubing with internal heating web.

FIG. 1 depicts a schematic of a fluid delivery system employing the present invention. An IV stand 100 supports a flexible container 102 which stores a fluid 104 such as blood or saline to be delivered to the patient. The fluid 104 feeds to a drip chamber 106 which accumulates the fluid before delivery to the patient. A tube 108 connecting the drip chamber 106 leads to a flow control valve 110 which regulates the flow rate of the fluid administered to the patient. A flexible tubing 112 connects the flow control valve 110 to a junction 114, which preferably includes a thermistor or other temperature sensor for detecting the initial temperature of the fluid. The junction 114 is connected electronically to a heat controlling unit 116 preferably mounted on the IV stand 100 as shown. The heat controlling unit 116 is powered by an AC current via its power line 118, or could alternatively be powered by a dc battery if necessary.

As fluid exits the junction 114, it travels along a tubing 120 to a cannula 122 or other means for introducing the IV fluid to the patient. Along this length of tubing 120, heat is continuously transferred to the fluid as will be explained in greater detail below. At or near the cannula 122, a second thermal sensor is provided which measures the temperature of the fluid immediately before the fluid's introduction into the patient, and this temperature is communicated back to the heat controlling unit 116. By adjusting the amount of heat which is introduced along the length of tubing 120, the fluid temperature can be accurately controlled and delivered at the proper temperature. In this manner, a contributor to hypothermia is diminished or eliminated.

Figure 2:
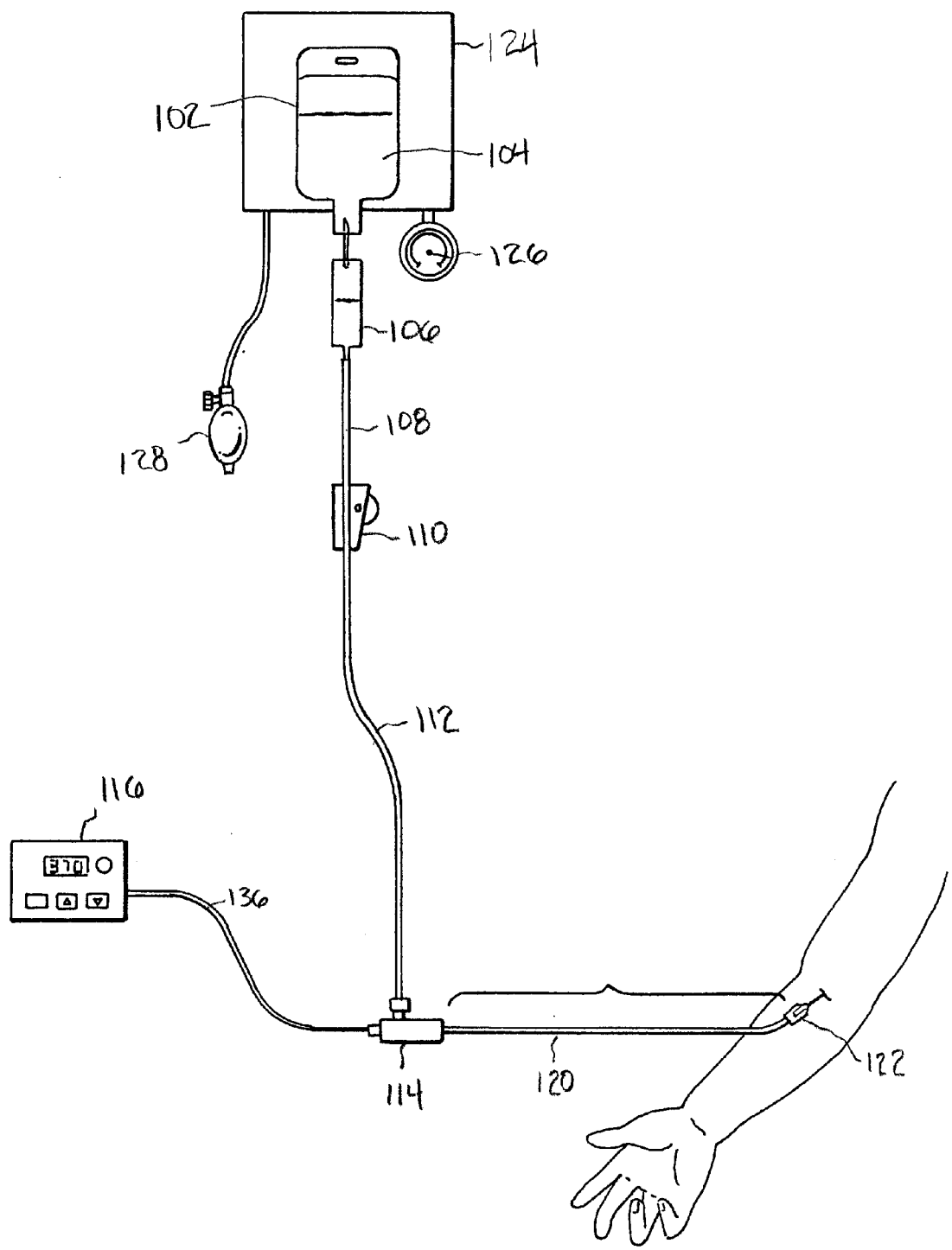
FIG. 2 is a second schematic illustration of a preferred embodiment of the present invention as previously depicted in FIG. 1 with a pressure assisted fluid flow.

FIG. 2 depicts a second embodiment to that shown in FIG. 1, in which the intravenous fluid 104 is delivered using pressure in addition to gravity to control the flow rate. Using like numerals to represent like components, FIG. 2 includes a pressure infuser 124 about the IV container 102 which imparts a pressure on the flexible container 102. A pressure gauge 126 attached to the pressure infuser 124 displays the pressure imparted on the container 102, which may be applied using either a manual delivery such as a hand pump 128, or a mechanical delivery such as a motor (not shown).

FIG. 3 shows a cross-section of the tubing 120, including devices to measure the fluid temperature and apply heat to the moving fluid. The junction 114 receives the cold fluid from the flow rate controller and a thermal sensor 130 in the junction 114 measures the temperature of the cold fluid. This first thermal sensor 130 senses overtemperature in the fluid, and can also be used to determine the initial power setting for heating the fluid. A flexible web 132 extends from the tubing 120 into the junction 114, where electrical leads 134 are connected. The electrical leads 134 extend from an electrically insulating conduit 136 and extend to the heat controlling unit 116 as previously shown in FIG. 1.

The tubing 120 further includes a second thermal sensor 138 at the proximal end (i.e., end nearest the patient), and the temperature measurements from the first and second thermal sensors are communicated back to the heat controlling unit 116 via the conduit 136. In a preferred embodiment, the proximal end includes a dual thermistor for redundancy, wherein a discrepancy between the two sensors forming the dual thermistor triggers an alarm that one of the thermistors has strayed from a predetermined tolerance. In this manner, a thermistor malfunction does not result in over-heated fluid being delivered to the patient. The tubing is preferably terminated at a "luer" connector 140, or similar attachment for facilitating the introduction of fluid into the patient.

FIG. 3 also details first and second electrodes 142, 143 positioned at opposite ends of the web 132, and connected by an electrical conduit 144 embedded in the web 132. The electrodes 142, 143 detect discontinuities that may occur in the web 132, such as breaks, pinholes, insulation failure, and bubbles forming on the web. The formation of bubbles can give rise to excessive power dissipation and hot spots on the web, which may in turn damage the tubing 120.

FIGS. 4 and 5 show the web element 132 disposed in the tubing 120. The tubing itself may be of the type traditionally used for IVs, such as one-eighth inch polyvinyl chloride (PVC) tubing. The web 132 is flexible and preferably extruded along with the embedded heating elements 146, from a heat-resistant material, and spans the diameter of the tubing as shown. The tubing 120 and web 132 may be extruded together in a single configuration, or the web may be formed separate from the tubing and subsequently inserted therein. Where the web and tubing are formed together, the web diametrically spans the tubing, integrally forming intersections with the walls of the tubing at opposite sides of the tubing.

The web includes wires 146 to electrically heat the web 132, which in turn heats the fluid continuously along the tubing 120. Alternately, the wires 146 may traverse the web laterally as well as longitudinally in a zigzag pattern to provide more heat per length of tubing. By passing current through the wires 146, the dissipation of power will cause the wires 146 to heat up along the entire length of the wires and consequently the web 132 is heated. As the fluid continuously flows past the web 132, the heat from the web is transferred to the fluid via conduction and convection. The web 132 also carries wires 150 which convey signals from the thermistors 130, 138, preferably along the central portion of the web. The web must be thin enough to allow the tubing to flex, but sturdy enough to prevent the web from cracking or splitting along the length of tubing. A typical width of the web is on the order of one tenth of an inch, and is preferably made from a plastic such as pvc or an extrudable elastomer.

Figure 6:
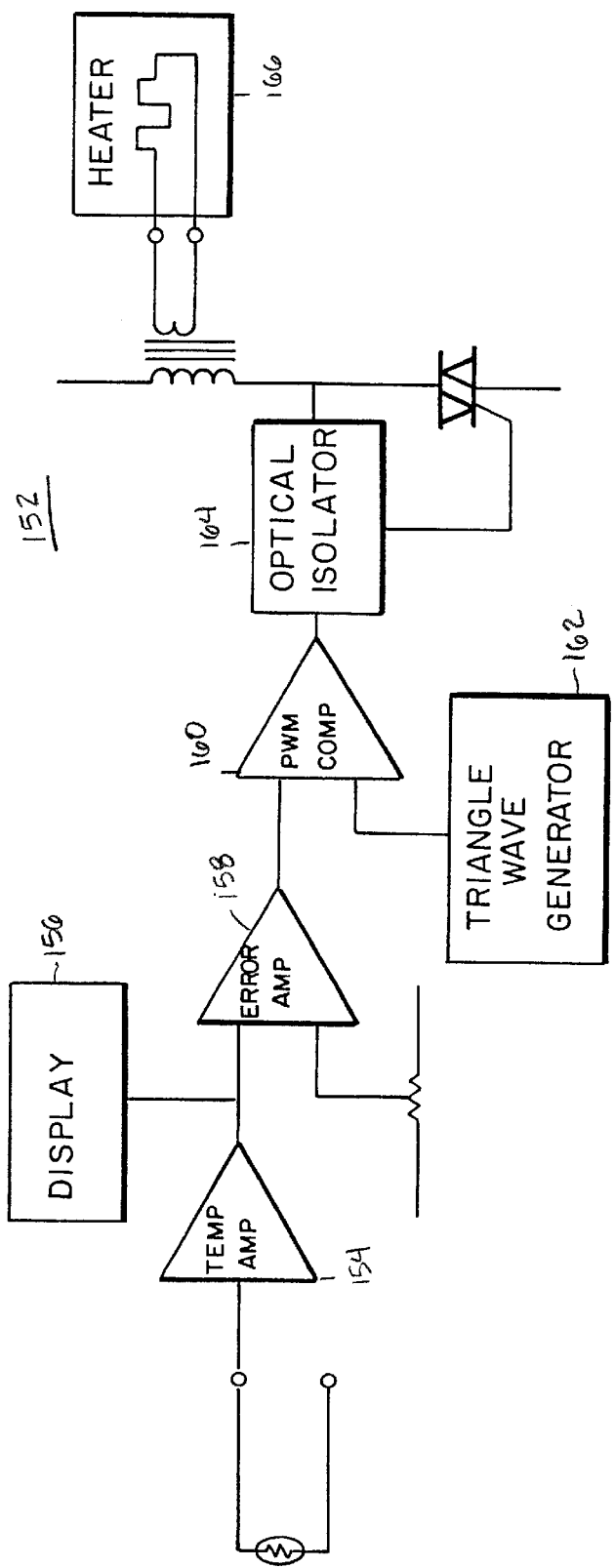
FIG. 6 is a block diagram of a heater controller used in the heating unit of the present invention.

FIG. 6 depicts a block diagram of a first embodiment feedback control circuit 152 employed by the present invention. The signal from the proximal thermistor is fed into an amplifier 154 which increases the signal strength, and the amplified signal is displayed at the display unit 156. The temperature signal is directed to an error amplifier 158, which receives the optimum or desired temperature from the heating unit input and compares the two signals. The difference is then supplied to a pulse width modulator (pwm) comparator 160, along with a known signal such as a triangle wave generated from a triangle wave generator 162, and the output of the comparator 160 is fed to an optical isolator 164. A heater transformer 166 is controlled by the output of the optical isolator 164, which in turn controls the amount of current generated in the heating wires 146 in the web 132. As more heat is needed, the power to the transformer is adjusted to augment the electrical current, raising the power delivered to the wire and producing more heat. The increase in the heat is transferred to the fluid, which raises the downstream temperature at the proximal thermistor. In this manner, the optimum temperature at the proximal thermistor is maintained.

FIG. 7 depicts a second feedback circuit comprising a dual microprocessor heat controller. In this circuit, signals from two proximal thermistors and one distal thermistor are converted to a digital signal via analog-to-digital converter 168 to a first microprocessor 170. In parallel, the three thermistor signals 172a, 172b, 172c are fed through a second analog-to-digital converter 174 along with a conductivity measurement 176, and the resultant digital signal 178 is directed to a second microprocessor 180 in communication with the first microprocessor 170. A display unit 182 and input device 184 are connected to the first microprocessor 170, which processes the digital signal and displays the temperatures at the display unit 182. The digital signals processed from the first and second microprocessors 170, 180 are each delivered to separate optical isolators 186a, 186b which test the signal using a primary triac and a secondary triac. The result of the test is used to adjust the power to the heater transformer 188, which in turn adjusts the current in the wires and the heat delivered to the fluid.

The disclosed heating system is a low mass, fast response time electrical heater that produces a flatter temperature versus flow characteristics profile as compared with fluid heaters using a heating jacket. Those skilled in the art will appreciate that various adaptations and modifications of the just-described preferred embodiment can be configured without departing from the scope and spirit of the invention. For example, the feedback control circuit could be modified from its described embodiments by those skilled in the art without departing from the scope of the invention. Similarly, other changes are possible while practicing the invention. Therefore, it is to be understood that, within the scope of the appended claims, the invention may be practiced other than as specifically described herein.

What is claimed is:

1. A system for delivering an intravenous liquid to a patient at a controlled temperature to address hypothermia comprising:

a flexible container for storing liquid where the liquid can be below a predetermined optimum delivery temperature:

a conduct tube connecting the flexible container for discharging the liquid from the flexible container;

a flow controller for controlling the flow of liquid from the flexible container through the conduit tube;

a first tubing connected to the flow controller;

a heat controlling unit;

a junction unit connected to the first tubing, the junction unit including an electrical connection member connecting said junction unit to the heat controlling unit;

a second tubing including a flexible web internally disposed inside the second tubing to extend substantially along the second tubing between the junction unit and the patient, the flexible web includes a heater member embedded within the flexible web to heat the flexible web as it extends along the second tubing which in turn heats the liquid flowing across the flexible web in the second tubing, the second tubing is connected to the junction unit to receive the liquid; and a heat sensor unit disposed inside the second tubing to measure the temperature of the liquid flowing through the second tubing, the heat controlling unit receives temperature signals from the heat sensor unit and adjusts a power current to the junction unit in response to the temperature signals, wherein the flexible web is in electrical communication with the junction unit to enable the heater member to convert the power current to heat which is transferred through the flexible web member to the liquid in the second tubing, the flexible web is an elongated flat solid insulating plastic member with embedded wires connecting the heat sensor unit with the junction unit.

2. The system of claim 1 where the heat sensor unit further includes a first temperature sensor disposed at a proximal location to the end of the second tubing where the intravenous fluid is to be delivered.

3. The system of claim 2 where the heat sensor unit further includes a redundant second temperature sensor disposed at the proximal location.

4. The system of claim 3 where the heat sensor unit further includes a distal temperature sensor disposed at a distal location to the end of the second tubing where the intravenous fluid is to be delivered.

5. The system of claim 1 wherein the flexible web includes a first heating conducting wire disposed along a first edge, and a second heat conducting wire disposed along a second edge, and a third wire communicating a temperature signal.

\* \* \* \* \*